US00PP09080P

United States Patent [19]

Hope

[11] Patent Number: Plant 9,080

[45] Date of Patent: Mar. 14, 1995

[54] ANTHURIUM PLANT NAMED PURA VIDA RED

[75] Inventor: Claude Hope, Cartago, Costa Rica

[73] Assignee: Ball Seed Company, Chicago, Ill.

[21] Appl. No.: 183,040

[22] Filed: Jan. 18, 1994

[51] Int. Cl.[6] ..... A01H 5/00
[52] U.S. Cl. ..... Plt./88.1
[58] Field of Search ..... Plt. 88.1

*Primary Examiner*—James R. Feyrer

*Attorney, Agent, or Firm*—Foley & Lardner

[57] ABSTRACT

A new and distinct cultivar of Anthurium plant named Pura Vida Red characterized by its non-fading dark red spathe color on both the top and under surfaces, yellow spadix color which similarly does not fade with maturity, relatively large flowers held above the foliage to provide a uniform display, flat flowers which do not curve inwardly, and its outwardly facing leaves which show the full leaf blade.

1 Drawing Sheet

The present invention comprises a new and distinct cultivar of Anthurium, botanically known as interspecific *Anthurium* hybrid, and referred to by the cultivar named Pura Vida Red.

The new cultivar is a product of a planned breeding program carried out by the inventor in Cartago, Costa Rica. The female parent was a selection from the cross between an unnamed *Anthurium amnicola* cultivar and an unnamed *Anthurium andreanum* cultivar, and the male parent was an unnamed cultivar of *Anthurium andreanum* characterized by its small leaves. The parents are proprietary cultivars used only in the breeding program.

The new cultivar was discovered from the progeny of the stated cross by the inventor in Cartago, Costa Rica, and given the number designation 179-14. Asexual propagation by divisions and micropropagated leaf cuttings first carried out by or under the supervision of the inventor in Cartago, Costa Rica, and later carried out in south central Florida and West Chicago, Ill., has demonstrated that the unique features of this new anthurium are stabilized and are reproduced true to type in successive propagations.

The following observations, measurements and values describe plants grown in south central Florida in a polypropylene-covered shade house with day temperatures of 30° to 38° C. and night temperatures of 20° to 30° C. Measurements and values represent averages for six typical plants observed for evaluation purposes.

The following traits have been repeatedly observed to be characteristics which in combination distinguish the new cultivar from other Anthuriums of the same general type, for example, the unpatented but well known commercial cultivar Lady Jane to which comparative reference is made.

1. The spathe color of Pura Vida Red is dark red compared to the medium pink spathe color of Lady Jane.

2. The dark red spathe color of the new cultivar is on both the top and underside of the spathe, unlike the spathe of Lady Jane wherein the underside color is a lighter shade of pink.

3. The inflorescence is long lasting. The spathe color does not fade or turn green with age, and the spadix maintains its yellow color as it matures.

4. Pura Vida Red has larger flowers than Lady Jane, with the flowers being held above the foliage in a uniform and showy display.

5. The flowers of Pura Vida Red are flat and do not curve inwardly.

6. The leaves face outwardly showing the full leaf blade.

A detailed comparison of Pura Vida Red and Lady Jane appears in Chart A at the end of the specification. In general comparison, the spathes of the new cultivar are substantially larger and dark red in color, compared to the pinkish-red spathe color of Lady Jane. The mature spadix color of the new cultivar is light yellow compared to the yellow-orange mature spadix color of Lady Jane.

All color references are to The Royal Horticultural Society Colour Chart (R.H.S.). Colors will vary somewhat depending on horticultural practices such as light level and fertilization rate, among others, without, however, any variation in genotype.

The color photographic drawing comprises a top perspective view showing the inflorescence and foliage of a typical specimen plant of the new cultivar.

The photograph is of a plant of the new cultivar grown in a 25.5 cm pot for one year from a tissue culture plug and grown under appropriate growing conditions. Colors are as accurate as possible with color illustrations of this type.

Origin: Seedling of unnamed parentage.

Classification: *Anthurium* hybrid, cv Pura Vida Red.

Propagation: Asexual production either by micropropagation, i.e., tissue culture, or division. Roots are initiated in approximately 21 days at 25° C. The rooting habit is epiphytic, roots emerge from stem, thick velamen.

Plant:

A. *Form.*—Upright.

B. *Habit of growth.*—Leaves produced in whorls.

C. *Foliage description.*—1. Size: a. Length: 24 cm. b. Width: 18 cm. 2. Shape: Cordate with two lobes on either side of petiole attachment. Apex is acuminate, base is truncate; leaves are oriented from slightly upright to perpendicular to petiole. 3. Surface texture: Leaf surfaces are smooth. Veins are slightly sunken on top side and protruding on under side. 4. Margin: Entire. 5.

Color: a. Young foliage top side: 146C. b. Young foliage under side: 147C. c. Mature foliage top side: 147A. d. Mature foliage under side: 147C. e. Older foliage top side: 137A. f. Older foliage under side: 147C. 6. Petiole: Length is 31 cm, diameter 5 mm; color 147A. 7. Venation: Color is same as color of top side of leaves and depends on leaf age; pattern is pinnate.

Inflorescence:

A. *Flower type and habit.*—Freely flowering.

B. *Natural flowering season.*—Year-round in tropical and subtropical areas.

C. *Flowers borne.*—At maturity, flowers are situated above foliage, arising from leaf axils. This feature is not clearly illustrated in the photographic drawing.

D. *Peduncle.*—Length is 38.5 cm, diameter 5 mm; color 147A.

E. *Quantity of flowers.*—Potential of one flower per leaf.

F. *Spathe.*—1. Shape: Cordate, apex cuspidate, base truncate; spathe is attached generally perpendicular to peduncle. 2. Size: a. Length: 8.5 cm. b. Width: 6.5 cm. 3. Color: a. Young spathe top side: 46A, shiny. b. Young spathe under side: 46A. c. Mature spathe top side: 46A. d. Mature spathe under side: 46A. e. Older spathe top side: 46A. f. Older spathe under side: 46A. 4. Surface texture: Top and under surfaces of spathe are smooth. However, veins are prominent, giving spathe a wavy texture. 5. Margin: Entire.

G. *Spadix.*—1. Shape: Cylindrical, tapering upwards. 2. Size: a. Length: 5.5 cm. b. Diameter base: 6 mm. c. Diameter center: 5 mm. d. Diameter tip: 3.5 mm. 3. Color: a. Young spadix top: 1C. b. Young spadix base: 1C. c. Mature spadix top: 10C. d. Mature spadix base: 11D. e. Older spadix top: 14D. f. Older spadix base: 154C. 4. Ovary size: 4 mm, square. 5. Anther size: 3 mm, square.

Disease resistance: No fungal, bacterial or viral problems have been observed to date.

CHART A

| CHARACTERISTIC | Pura Vida Lavender | LADY JANE |
|---|---|---|
| Young leaf color top side | 146A | 146A |
| Mature leaf color top side | 147A | 139A |
| Older leaf color top side | 139A | 139A |
| Young spathe color top side | 62B and 62D | 51B |
| Young spathe color under side | 62D | 51D |
| Mature spathe color top side | 62C and 69B | 51B |
| Mature spathe color under side | 155C | 51D |
| Older spathe color top side | 146D | 51C |
| Older spathe color under side | 146D | 144A |
| Spathe size width by length | 4 cm by 8.0 cm | 3.5 cm by 7 cm |
| Young spadix color top | 62A | 11D |
| Young spadix color base | 62A | 32C |
| Mature spadix color top | 62B | 18D |
| Mature spadix color base | 62C | 18B |
| Older spadix color top | 144C | 144A |
| Older spadix color base | 144C | 144A |

It is claimed:

1. A new and distinct cultivar of Anthurium plant named Pura Vida Red, as illustrated and described.

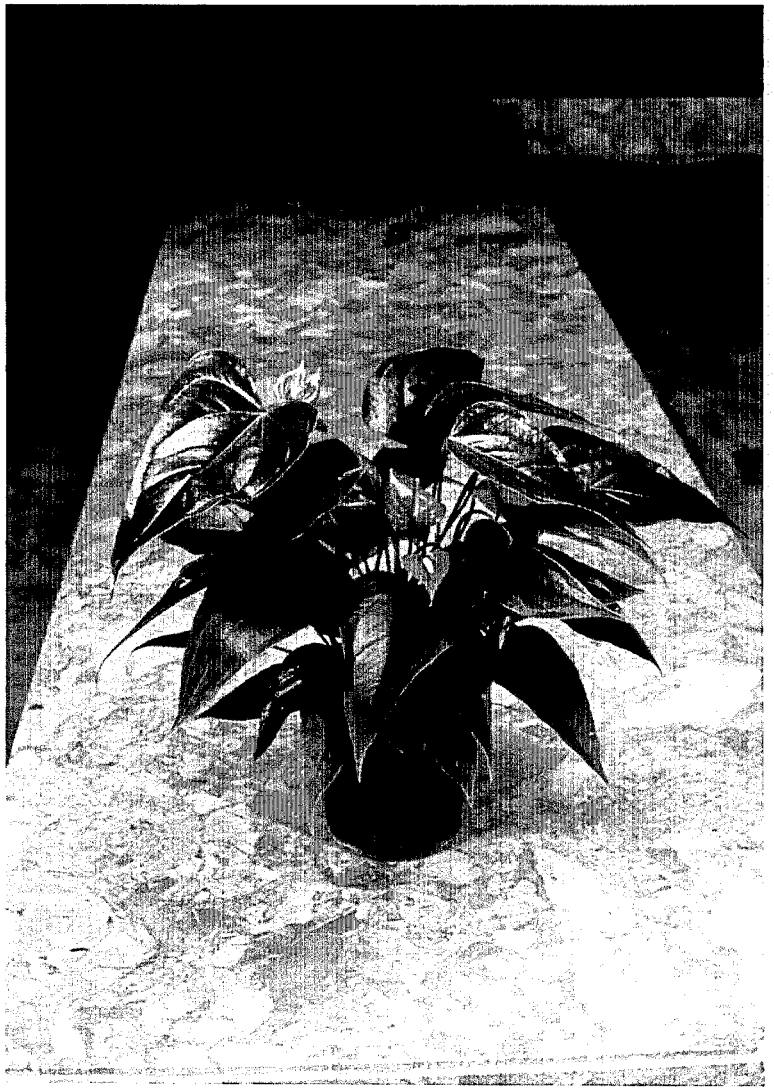

* * * * *